United States Patent [19]
Davies et al.

[11] Patent Number: 6,008,227
[45] Date of Patent: Dec. 28, 1999

[54] PROCESS FOR BLOCKING 5-HT AND DOPAMINE UPTAKE WITH BIOLOGICALLY ACTIVE TROPANE DERIVATIVES

[75] Inventors: Huw M. L. Davies, Clemmons; Steven R. Childers; Barbara Bennett, both of Winston-Salem, all of N.C.

[73] Assignee: Wake Forest University, Winston-Salem, N.C.

[21] Appl. No.: 08/063,431

[22] Filed: May 18, 1993

Related U.S. Application Data

[63] Continuation-in-part of application No. 07/851,090, Mar. 13, 1992, Pat. No. 5,262,428.

[51] Int. Cl.$^6$ ................................................ A61K 31/44
[52] U.S. Cl. .............................. 514/304; 514/299; 514/80
[58] Field of Search .................................. 514/304, 299, 514/80

[56] References Cited

U.S. PATENT DOCUMENTS

| | | | |
|---|---|---|---|
| 3,120,537 | 2/1964 | Archer et al. | 546/124 |
| 3,813,404 | 5/1974 | Clarke et al. | 260/292 |
| 5,128,118 | 7/1992 | Carroll et al. | 424/1.1 |

OTHER PUBLICATIONS

Lewin et al., Journal of Medicinal Chemistry, vol. 35, No. 1 (1992) pp. 135–140.

Abraham et al., Hournal of Medicinal Chemistry, vol. 35, No. 1 (1992) pp. 141–144.

Kozikowski et al., Medicinal Chemistry Research, vol. 1 (1991) pp. 312–21.

Davies et al., J. Organic Chemistry, vol. 56, No. 19 (1991) pp. 5696–5700.

Madras, et al., Molecular Pharmacology, 36:518–524 (1989).

Davies, et al., Tetrahedron Letters, vol. 30, No. 35, pp. 4653–4656 (1989).

Boja, et al., European Journal of Pharmacology, 184 (1990), pp. 329–332.

Carroll, et al., Journal of Medicinal Chemistry, vol. 34, No. 9 (1991), pp. 2719–2725.

Clarke, et al., Journal of Medicinal Chemistry, vol. 16, No. 11 (1973) pp. 1260–1267.

Davies et al., American Chemical Society, Dec. 5–7, 1990, pp. 181–182.

Ritz, M. C. et al. "Cocaine Inhibition of Ligand Binding . . . " Life Sciences, vol. 46, No. 9, 1990, pp. 635–654.

*Primary Examiner*—M. Moezie
*Attorney, Agent, or Firm*—Zarley, McKee, Thomte, Voorhees & Sease

[57] ABSTRACT

Selective blockade of DA and 5-HT uptake sites with 3-aryltropane derivatives.

16 Claims, 2 Drawing Sheets

PROCESS FOR BLOCKING 5-HT AND DOPAMINE UPTAKE WITH BIOLOGICALLY ACTIVE TROPANE DERIVATIVES

CROSS-REFERENCED TO A RELATED APPLICATION

This application is a continuation-in-part of, commonly assigned application, Davies, et al, Ser. No. 07/851,090, entitled BIOLOGICALLY ACTIVE TROPANE DERIVATIVES, filed Mar. 13, 1992 now U.S. Pat. No. 5,262,428.

GRANT REFERENCE

This invention was made with government support under R01-DA-6301-02 and P50-DA06634 awarded by the National Institute on Drug Abuse. The government has certain rights in the invention.

BACKGROUND OF THE INVENTION

The tropane skeleton is a basic structural unit that can lead to compounds with diverse Central Nervous System (CNS) activity. Due to the rigid nature of the structure, the possibility exists for the preparation of highly selective compounds. This application describes the synthesis of tropane derivatives that selectively bind to monoamine neurotransmitters and thus have the potential for the treatment of major depression, Parkinson's disease and attention-deficit hyperactivity disorder (ADD).

Two important central nervous system neurotransmitters are serotonin (5-HT) and dopamine (DA). Together with norepinephrine and epinephrine, these neurotransmitters comprise the group of agents known as the monoamines. Either 5-HT or DA have been implicated in a variety of disorders, including depression, Parkinsons disease, ADD, obesity and cocaine addiction.

Major depression represents one of the most common mental illness, affecting between 5–10% of the population. The disease is characterized by extreme changes in mood which may also be associated with psychoses. It has generally been found that most antidepressant agents exert significant effects on the regulation of monoamine neurotransmitters, including DA, 5-HT and norepinephrine. The tricyclic antidepressants, such as imipramine, are the most commonly used drugs for the treatment of depression. Their ability to inhibit the neuronal uptake of norepinephrine is believed to be a major factor behind their efficacy.

A number of new types of antidepressants have been developed in recent years. Two such compounds that are marketed in the U.S. are trazodone and fluoxetine. Both of these compounds interact with the regulation of 5-HT. Trazodone potentiates the actions of 5-HT while fluoxetine is a potent and selective inhibitor of 5-HT reuptake. 3-Chloroimipramine which inhibits both 5-HT and norepinephrine reuptake has been extensively used as an antidepressant in Europe and Canada. Other compounds which are of current interest or have been examined as antidepressants include fluvoxamine, citalopram, zimeldine, bupropion and nomifensine. All of these drugs inhibit monoamine uptake mechanisms, but differ in selectivity between the dopamine, 5-HT and norepinephrine transporters.

Other syndromes also respond to antidepressant drugs. These include (1) severe anxiety syndromes characterized by panic reactions, and (2) obsessive-compulsive disorder, both of which seem most likely to respond to 5-HT selective agents. Monoamine uptake blockers have also been useful in treatment of chronic pain, neuralgias, migraine, sleep apnea, fibromyalgia, and irritable bowel syndrome.

Parkinson's disease effects about 1% of the population over the age of 65 and leads to serious neurological disorders. The main clinical features of the disease are centered around disruption of motor function, such as walking, speech, eating and other skilled acts. It has been recognized that the disease is the result of dopamine deficiency in the basal ganglia. Thus, drugs that can increase the levels of dopamine have the potential to be effective medications for the treatment of Parkinson's disease. The most effective drug in this regard has been levodopa which acts as a biogenic precursor to dopamine.

Considerable attention has recently been directed to the condition known as attention-deficit hyperactivity disorder. Children with this condition tend to be very active physically but have great difficulty with situations requiring long periods of attention. Consequently, they tend to underachieve academically and can be very disruptive. Furthermore, these behavioral problems often persist in modified forms into adulthood. The condition appears to be associated to the effect of monoamines in the cerebral cortex, which are involved with control of attention. A number of stimulant drugs such as dextroamphetamine, methylphenidate as well as the tricyclic antidepressants, antipsychotic agents and clonidine have been used as medications to control the disorder. Many of these drugs interact with the monoamine uptake transporters.

Another disorder for which inhibitors of monoamine transport are useful therapeutic agents is obesity. In general, sympathomimetic drugs (i.e., those which increase synaptic levels of monoamines) promote weight loss by suppressing appetite. Drugs like mazindol, which act as sympathomimetic agents by blocking monoamine uptake, have been useful in the treatment of obesity.

Cocaine has the following formula:

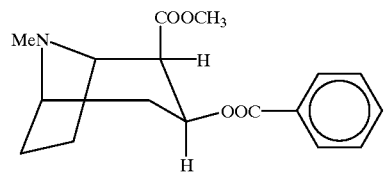

The basic ring structure of cocaine is a tropane ring system.

It has previously been shown that cocaine and related compounds are potent inhibitors of dopamine reuptake and this may lead to compounds with reinforcing properties. In recent years a number of new extremely potent cocaine analogs have been prepared based on the tropane structure (Abraham et al., *Journal of Medicinal Chemistry* 1992, 35, 141; Boja et al., *European Journal of Pharmacology*, 1990, 183,329; Boja et al., *European Journal of Pharmacology*, 1991, 194, 133; Carroll et al., *Journal of Medicinal Chemistry*, 1992, 35, 969; Carroll et al., *Journal of Medicinal Chemistry*, 1992, 35, 1813; Carroll et al., *Journal of Medicinal Chemistry*, 1992, 35, 2497, Cline et al., *Journal of Pharmacology and Experimental Therapeutics*, 1992, 260, 1174; Cline et al., *Synapse*, 1992 12, 37; Kozikowski et al., *Medicinal Chemistry Research*, 1991, 1, 312; Kozikowski et al., *Journal of Medicinal Chemistry*, 1992, 35, 4764; Lewin et al., *Journal of Medicinal Chemistry*, 1992, 35, 135; Madras et al., *Molecular Pharmacology*, 1989, 36, 518). All of these compounds are based on the tropane skeleton and tend to selectively bind to the dopamine transporter. Certain structural variations can lead to compounds that bind with very high selectivity to the dopamine reuptake site (Carroll et al, *Journal of Medicinal Chemistry*, 1992, 35, 2497). However, all of these tropane derivatives are very similar to each other because they are all derived from cocaine as starting material.

It has now been discovered that if the tropane ring system is modified, particularly at the aryl moiety as hereinafter described, compounds can be produced which are more selective in binding to 5-HT transporters as compared to DA transporters. Since these modified tropanes (as described below) bind preferentially to the 5-HT transporter, they may preferentially block 5-HT transport, thus, increasing synaptic levels of 5-HT. This may be helpful in treating diseases related to 5-HT function. Similarly, tropane analogs can be synthesized which selectively block DA transporters and selectively increase synaptic levels of DA.

In principle, the tropane skeleton is ideally suited to prepare highly selective compounds because it is a rigid structure and tropane derivatives will have rather limited conformational flexibility. Such derivatives may be altered by appropriate structural changes so that analogs favoring binding to either the 5-HT or DA reuptake site could be prepared. The novel chemistry that has been developed, as referred to in our parent application, has enabled preparation of a much wider range of tropane analogs than was previously accessible, leading to novel structures with selective biological activity.

Accordingly, it is a primary objective of the present invention to provide a process for preparing tropane analogs which are selective inhibitors of either 5-HT or DA reuptake.

Another primary objective of the present invention is to prepare a range of tropane analogs which can be investigated as drugs for the treatment of chronic depression.

A still further objective of the present invention is to provide a wide range of tropane derivatives which can be systematically used and tested to determine structure-activity relationships for binding at dopamine, 5-HT and norepinephrine transporters.

A further objective is to provide a treatment system for diseases whose course can be altered by patient treatment with compounds that selectively bind to either the 5-HT or DA reuptake site and therefore prevent neurotransmissions at this site.

SUMMARY OF THE INVENTION

Biologically active derivatives of the tropane ring system are provided which selectively bind either to the 5-HT or DA reuptake site, leading to compounds which have use for treatment of clinical depression, Parkinson's Disease, ADD and obesity.

DETAILED DESCRIPTION OF THE INVENTION

Figure 1:
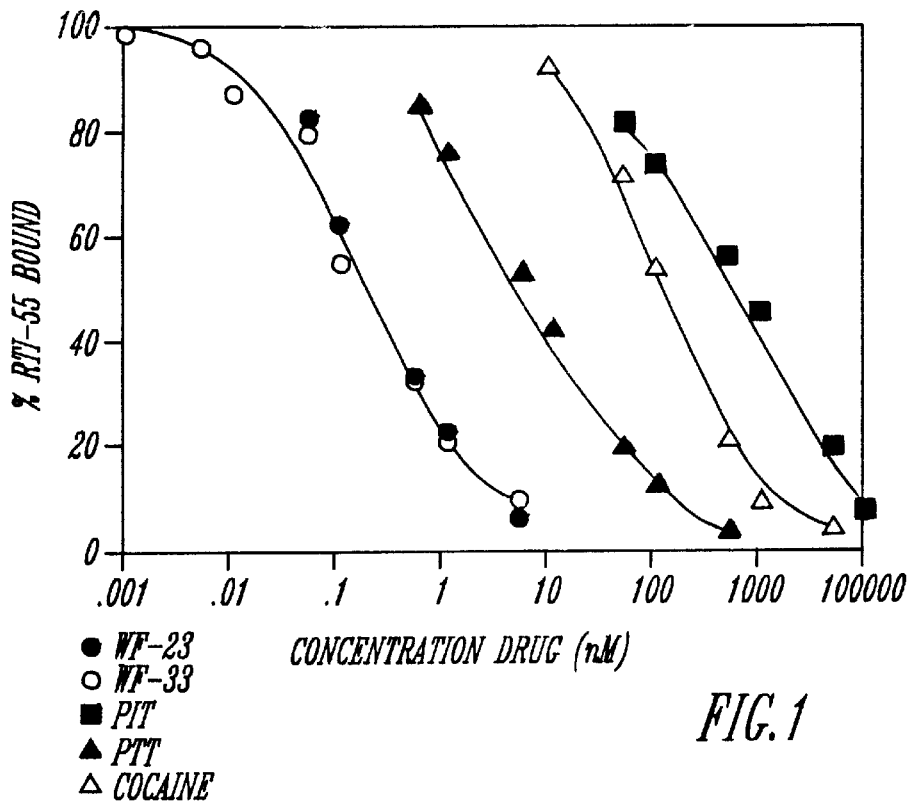
FIGS. 1, 2, 3, & 4, show the potencies of various analogs of the present invention 5-HT and DA in binding to transporters. These results demonstrate analogs with three different categories of selectivity: DA-selective, 5-HT selective and non-selective.

The focus of this application will be on uses of tropane derivatives of the general formula:

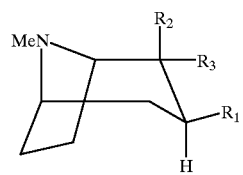

Wherein $R_1$ is an aromatic moeity and may be any 1-naphthyl, 2-naphthyl, phenyl, $C_1$ to $C_8$ alkylaryl or indole moiety. Preferred are isopropylphenyl and naphthyl. $R_2$ and $R_3$ may be as follows: Only one of $R_2$ and $R_3$ can be hydrogen at the same time and each of $R_2$ and $R_3$ can be a ketone moiety,

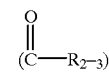

an ester moiety,

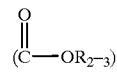

a phosphonate, a sulfone moiety, a cyano, an oxazole, or a imidazole. It is preferred that $R_2$ and $R_3$ be selected from ketone moieties or ester moieties, preferably $C_1$ to $C_8$ alkyl or alkoxy. If desired the $M_e$ group may be more generally described as $R_4$ which may be hydrogen or lower ($C_1$ to $C_8$) alkyl.

The very most preferred compounds for use in the present process are:
Wherein R is $C_1$ to $C_8$ and Ar is an aryl moiety as earlier defined.

The synthesis of the tropane derivatives was achieved by the general scheme shown below. The experimental procedure for the final step has been described in detail in the original patent. The details of the earlier steps have been reported (Davies, et al., *Journal of Organic Chemistry*, 1991, 56, 5696).

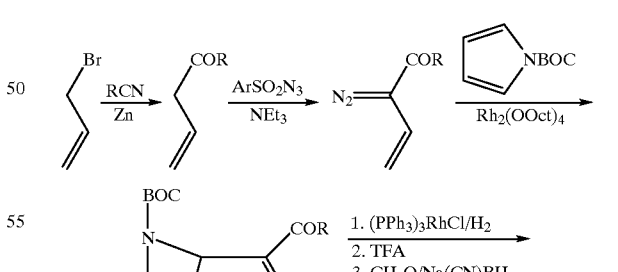

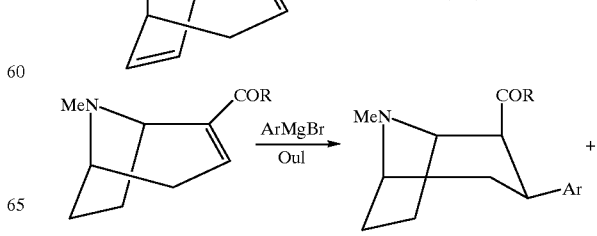

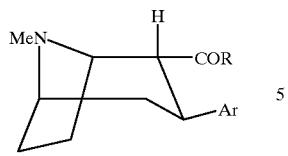

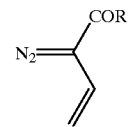

This basic process is described in our earlier cross-referenced parent application. Basically, in the process of that case, 3-aryltropane derivatives are prepared by reacting 8-azabicyclo[3.2.1]oct-2-ene with an aryl Grignard reagent in the presence of catalytically effective amounts of copper (I) and/or copper (II) salts. The 3-aryl-tropane derivative starting material can be conveniently prepared by decomposing functionalized vinyldiazomethanes in the presence of certain pyrroles, preferably in substantial excess of the stoichiometric amount, using a decomposition catalyst, preferably a rhodium catalyst. The catalyst may also be a copper, palladium or silver salt catalyst. This provides a bicyclic intermediate containing the basic tropane ring system which is thereafter converted to an 8-azabicyclo [3.2.1]oct-2-ene, which itself may be used as a starting material to react with an aryl Grignard reagent in providing the synthesis route to the unique cocaine analogs of the present invention.

The starting material of the process is, namely the 8-azabicyclo[3.2.1]oct-2-ene, and has the following formula:

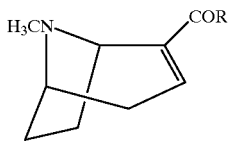

In the above formula R is selected from the group consisting of $C_1$ to $C_8$ alkyl and $C_1$ to $C_8$ oxyalkyl. In other words, the two position moiety may be functionally substituted by ketone groups or ester groups.

One of the present inventors, namely Dr. Huw M. L. Davies, has previously published concerning the general synthesis used for the starting material of the parent case, namely synthesizing 8-azabicyclo [3.2.1]oct-2-ene of the above formula. In this regard see, Davies, et al., "Novel Entry to the Tropane System by Reaction of Rhodiumi (II) Acetate Stabilized Vinylcarbenoides with Pyrroles," *Tetrahedron Letters*, vol. 30, no.35, pp. 4653–4656, (1989) a December 1990 abstract of a regional ACS meeting held in New Orleans, entitled Davies, et al., "Chemistry of Vinylcarbenoids with a Single Electron Withdrawing Group, an Approach to Tropane Alkaloids", American Chemical Society, Dec. 5–7, 1990, pp. 181–182; Davies, et al., "Synthesis of ± Ferruginine and Anhydro-ecgonine Methyl Ester by a Tandem Cyclopropanation/Cope Rearrangement", Journal of Organic Chemistry, 1991, Vol. 56, pp. 5696–5700. The subject matter of each of these publications of Davies et al is incorporated herein by reference and therefore need not be described in full detail. However, certain preferred process operations, not specifically mentioned in the above articles, are described herein for sake of completeness.

Preparation of the starting material for the Grignard addition of the present invention, namely, preparation of 8-azabicyclo[3.2.1]oct-2-ene as above described employs in its first step a process of decomposing of a functionalized vinyldiazomethane of the formula:

in the presence of at least a stoichiometric amount of a pyrrole of the formula:

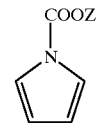

wherein Z is a functional group protector, and also in the presence of a small but effective amount of a decomposition catalyst selected from the group consisting of rhodium, copper, palladium and silver salts, to provide an intermediate bicyclic compound.

R as shown above represents a $C_1$ to $C_8$ alkyl or $C_1$ to $C_8$ oxyalkyl. Preferably R is an alkyl and therefore as explained herein after, the resulting analog of cocaine ultimately prepared will have a ketone group at the two position. In the pyrrole, Z represents a functional group protector such as trimethylsilylethyl, although it is understood that other classic protecting groups such as tertiarybutyl group may also be employed.

The amount of the pyrrole for this first reaction scheme needs to be at least a stoichiometric amount in comparison with the vinyldiazomethane and preferably is in excess of the stoichiometric amount, perhaps within the range of a two-fold to a five-fold excess. An excess is preferred in terms of achieving the desired high yields of the bicyclic intermediate because the vinyldiazomethane is decomposed to a very reactive intermediate, namely a vinylcarbenoid which will, unless it is trapped by use of stoichiometric excesses of the pyrrole, rapidly decompose.

The pyrroles above described can be conventionally prepared using well known chemistry as described in the Journal of Organic Chemistry, 1991, vol. 56 article, of the author earlier cited. The reaction is preferably run at a temperature of within the range of from 25° C. to about 100° C., preferably at about 80° C. The reaction can be run at 25° C. if there is slow addition of the vinyldiazomethane to the pyrrole. The pressure is not critical in this reaction step.

As explained above, the reaction is conducted in the presence of a decomposition catalyst selected from the group consisting of rhodium, copper, palladium and silver salts. Preferably the catalyst is a rhodium salt catalyst and may be a rhodium (II) acetate, mandelate, trifluoroacetate, hexanoate, pivalate or octanoate. The presently most preferred catalyst is rhodium octanoate which seems to allow higher yields of desired product. The amount of catalyst may vary from 0.25 mole per cent to about 2.0 mole per cent of the vinyldiazomethane, and is preferably about 1.0 mole per cent of the amount of the vinyldiazomethane reactant.

Reaction time does not appear to be critical and the time may vary from a few minutes up to several hours if drop wise addition is accomplished. The other carbon atoms of the 8-azabicyclo[3.2.1]oct-2-ene can include substituents other than hydrogen (e.g. one or more of the other carbon atoms of the bicyclic system can include a lower alkyl substituent group) because a more highly substituted pyrrole or vinyldiazomethane may be used as starting material.

This first step reaction produces an intermediate bicyclic compound which upon hydrogenating, removal of the deprotective group and reductive methylation is converted to the earlier described 8-azabicyclo [3.2.1]oct-2-ene. The hydrogenation, deprotecting and reductive methylation are all well known steps and need not be described herein.

Where R equals methyl and the protecting group used is trimethylsilyl the intermediate is methyl 8-(2-(trimethyl-silyl)ethoxycarbonyl)-8-azabicyclo [3.2.1]octa-2,6-dien-2-oate.

This reaction is preferably conducted in the presence of a solvent and the solvent is preferably a non-polar solvent. Suitable non-polar solvents for conducting this reaction may be pentane, hexane, and benzene. Other suitable non-polar solvents, capable of dissolving the basic reactants may also be employed, with the precise solvent not being critical, as long as it is in fact non-polar.

For details of the hydrogenating, deprotecting and reductive methylation see, the previously incorporated by reference 1991 vol. 56, Journal of Organic Chemistry article. There it is basically described that the catalytic hydrogenation is a process employing a Wilkinson's catalyst and that deprotection occurs with, for example, tertiarybutyl ammonium flouride to give the desired 8-azabicyclo [3.2.1]oct-2-ene at yields as high as 95%. As explained in the earlier referenced article, the composition is purified by silica gel column chromatography.

The 8-azabicyclo[3.2.1]oct-2-ene is then used as a starting material for the process of the present invention. It has been found that the 8-azabicyclo [3.2.1]oct-2-ene formula earlier described, can be converted to biologically active cocaine analogs having a wide variety of active analog structures by reacting with a aryl Grignard reagent in the presence of a catalytically effective amount of a copper salt catalyst. The copper salt catalyst may be a copper (I) or copper (II) catalyst.

As previously described, it is preferred that the R group of the 8-azabicyclo[3.2.1]oct-2-ene be $C_1$ to $C_8$ alkyl, rather than an oxyalkyl since it is preferred that the two substituent be a ketone substitution rather than an ester substitution. The ketones behave better in the copper catalysed reaction, and as explained later in the biological activity section of the specification, should have higher metabolic stability and have equivalent binding site activity. The Grignard addition reaction is run in a suitable non-polar organic solvent, preferably ether or tetrahydrofuran.

The Grignard reagent (ArMgX) may be any suitable aryl magnesium halide. The aryl group may be phenyl, substituted phenyl, $C_1$ to $C_8$ alkylaryl, polyaryl such as naphthyl, anthracyl or alkylpolyaryl. Alkyl magnesium halides ($C_1$ to $C_8$) may also be used. The "X" moiety represents a halide group and is preferably bromide. The copper salt may be a copper (I) or (II) salt and can be, for example, copper bromide dimethyl sulfide. The amount of the Grignard reagent is preferably an excess of the stoichiometric amount in order to assure completion of the reaction. Suitable high yields are obtained when an excess of up to four-fold of the Grignard reagent is employed. The amount of the copper salt catalyst can be from 5% (molar) to 20% (molar) of the Grignard reagent, and is preferably 15 mole percent of the amount of the Grignard reagent. The reaction to produce the desired ketone is represented by the following equation reaction:

As seen the reaction product is a mixture of two structural isomers, one with the 2-moiety position upwardly (a) and the second with the 2-moiety position downwardly. (b) Those analogs that are most preferred are the analogs wherein R is alkyl and therefore the two position moiety is a ketone moiety, and that the structural isomer is with the ketone groups in an up position. These are far more active in binding assays, than the downward structural isomers and in some instances as much as 200 times more active in site-binding.

Certain other process conditions are worthy of mention. The reaction is not temperature critical and may be run at anything from 0° C. or lower up to room temperature, or even higher. The reaction is preferably run under an inert gas atmosphere. The reaction is substantially immediate and therefore may be run from a few minutes to as much as twelve hours. Preferably the reaction occurs under stirring in order to assure completeness. After completion the reaction can be quenched with for example HCl/ice, with the desired compound extracted with ether. It may be purified as illustrated in the examples by conventional silica gel chromatography.

The compounds may be administered orally, parenterally or intravenously. The preferred route of administration is oral. The dose levels may be from 4 micrograms per kilogram of body weight up to 50 milligrams/kg of body weight and more typically from 20 micrograms/kg up to 15 mg/kg.

The novel tropane analogs synthesized by the vinylcarbeonoid scheme listed above were tested for their ability to interact with 5-HT and dopamine transporters by two assays: displacement of radioligand binding to transporter sites, and direct inhibition of 5-HT or dopamine uptake in acutely dissociated fetal and adult rat neurons. These assays are known to correlate with transport sites in human brain. In binding studies, low concentrations (10–20 pM) of [$^{125}$I] RTI-55, the potent tropane analog recently synthesized by Carroll's group (Boja et al., *European Journal of Pharmacology*, 1991, 184, 329), was used to label dopamine transporters in rat striatal membranes, while [$^3$H]paroxetine (Harbert et al., *European Journal of Pharmacology*, 1985, 118, 107) was used to label 5-HT transporter sites in rat frontal cortex. Up to the present time, 34 analogs have been tested for binding; their potencies in binding and uptake assays are summarized in Table 1 below.

TABLE 1

Tropane analogs: potencies in transporter binding and uptake assays

| Drug | R1 | R2 | R3 | [$^{125}$I]RTI-55 K1 (nM) | [$^3$H] paroxetine K1 (nM) | binding ratio | DA uptake IC$_{50}$ (nM) | 5-HT uptake IC$_{50}$ (nM) | uptake ratio |
|---|---|---|---|---|---|---|---|---|---|
| cocaine | COOPh | COOCH$_3$ | H | 173 ± 19 | 302 ± 22 | 1.75 | 187 ± 11 | 591 ± 48 | 3.2 |
| WF-1 | Ph-pF | H | COCH$_3$ | 929 ± 160 | >10,000 | — | | | |
| WF-2 | Ph | H | COCH$_3$ | 7270 ± 1210 | >10,000 | — | | | |
| WF-3 | Ph-pCH$_3$ | H | COCH$_3$ | 775 ± 57 | >10,000 | — | | | |
| WF-4 | Ph-pCH$_3$ | COCH$_3$ | H | 9.8 ± 0.5 | 122 ± 22 | 12.4 | 13.8 ± 2.6 | 330 ± 75 | 24 |

TABLE 1-continued

Tropane analogs: potencies in transporter binding and uptake assays

| Drug | R1 | R2 | R3 | [$^{125}$I]RTI-55 K1 (nM) | [$^3$H] paroxetine K1 (nM) | binding ratio | DA uptake IC$_{50}$ (nM) | 5-HT uptake IC$_{50}$ (nM) | uptake ratio |
|---|---|---|---|---|---|---|---|---|---|
| WF-5 | Ph | COCH$_3$ | H | 114 ± 22 | | | | | |
| WF-6 | Ph | H | COOCH$_3$ | 2060 ± 545 | >10,000 | — | | | |
| WF-7 | Ph-pF | COCH$_3$ | H | 70.8 ± 13 | 857 ± 187 | 12.1 | | | |
| WF-8 | 1-naphthyl | COCH$_3$ | H | 10.1 ± 2.2 | 25.6 ± 5.1 | 2.53 | 20.7 ± 7.7 | 4.55 ± 0.040 | 0.220 |
| WF-9 | Ph-pCH$_2$CH$_3$ | COCH$_3$ | H | 152 ± 24 | 78.2 ± 22 | 0.51 | 1160 ± 266 | 9.5 ± 5.4 | 0.0082 |
| WF-10 | Ph | COOCH$_3$ | H | 98.8 ± 12.2 | 1290 ± 51 | 13.1 | | | |
| WF-11PTT | Ph-pCH$_3$ | COCH$_2$H$_3$ | H | 8.2 ± 1.6 | 131 ± 10 | 15.9 | 2.21 ± 1.7 | 310 ± 104 | 140 |
| WF-13 | Ph-PCH$_3$ | H | COCH$_2$CH$_3$ | 764 ± 84 | >10,000 | ND | | | |
| WF-14 | CH$_2$CH$_3$ | H | COCH$_2$CH$_3$ | >50,000 | >10,000 | — | | | |
| WF-15 | 1-naphthyl | COCH$_3$ | H | 97.0 ± 21 | | | | | |
| WF-16 | Ph-pCH$_2$CH$_3$ | H | COCH$_3$ | 2290 ± 360 | >10,000 | — | | | |
| WF-17 | Ph-pCH$_3$ | H | COCH(Me)$_2$ | 2130 ± 266 | >10,000 | — | | | |
| WF-18 | CH$_2$CH$_3$ | COCH$_2$CH$_3$ | H | >50,000 | | | | | |
| WF-19 | cyclohex | COCH$_2$CH$_3$ | H | 4610 ± 492 | >10,000 | — | | | |
| WF-21 | PhoCH$_3$ | H | COCH$_2$CH$_3$ | 1287 ± 322 | >10,000 | — | | | |
| WF-22 | PhoCH$_3$ | COCH$_2$CH$_3$ | H | 814 ± 220 | 1056 ± 395 | 1.30 | | | |
| WF-23 | 2-naphthyl | COCH$_2$CH$_3$ | H | 0.20 ± 0.04 | 0.63 ± 0.20 | 3.1 | .027 ± 0.016 | 0.27 ± 0.13 | 10.0 |
| WF-23(1) | 2-naphthyl | COCH$_2$CH$_3$ | H | 113 ± 26 | 484 ± 146 | 4.2 | | | |
| WF-23(2) | 2-naphthyl | COCH$_2$CH$_3$ | H | 0.032 ± 0.007 | 0.127 ± 0.05 | 3.96 | | | |
| WF-24 | 2-naphthyl | H | COCH$_2$CH$_3$ | 2.51 ± 0.82 | 16.4 ± 2.0 | 6.53 | 5.9 ± 2.4 | | |
| WF-25 | Ph | COCH$_2$CH$_3$ | H | 48.3 ± 2.8 | 1005 ± 112 | 20.8 | | | |
| WF-26 | Ph-p(CH$_3$)$_3$ | COCH$_2$CH$_3$ | H | 2120 ± 630 | 1771 ± 474 | 0.84 | | | |
| WF-27 | 4CH$_3$-1-naph | COCH$_2$CH$_3$ | H | 25.1 ± 0.5 | 8.99 ± 1.71 | 0.358 | 260 ± 98 | 14.6 ± 10.6 | 0.056 |
| WF-29 | Ph-pF | COCH$_2$CH$_3$ | H | 15.3 ± 2.8 | | | | | |
| WF-30 | 1-naphthyl | COCH$_2$CH$_3$ | H | 5.34 ± 1.27 | 20.9 ± 2.9 | 3.91 | 3.66 ± 1.91 | 5.43 ± 4.63 | 1.46 |
| WF-31PTT | PhCH(CH$_3$)$_2$ | COCH$_2$CH$_3$ | H | 615 ± 98 | 54.5 ± 8.9 | 0.089 | 5840 ± 2600 | 46.9 ± 37.1 | 0.0082 |
| WF-32 | 2-naphthyl | COCH$_3$ | H | 0.248 ± 0.15 | 1.06 ± 0.36 | 4.27 | | | |
| WF-33 | 6MeO-2naph | COCH$_2$CH$_3$ | H | 0.130 ± 0.036 | 2.24 ± 0.35 | | | | |
| WF-34 | 6MeO-2naph | H | COCH$_2$CH$_3$ | 54.7 ± 15 | 206 ± 81 | 3.76 | | | |
| WF-35 | Ph-pPh | COCH$_2$CH$_3$ | H | 2.29 ± 1.1 | 4.31 ± 0.01 | 1.88 | | | |

In Table 1, the general formula is that depicted in the earlier part of this application, just at the beginning of the heading Detailed Description of the Invention. Code names, as presented, WF-1 through WF-35, are internal names of the assignee and simply stand for "Wake Forest-1" etc. Two analogs have been assigned trivial abbreviations: WF-11 is PTT, and WF-31 is PIT.

The binding affinity of tropane derivatives at the dopamine transporter was the basis of the original patent on drugs for the treatment of cocaine addiction. In the original application, the binding affinities for WF 1–5, 7–9, 11 were reported as background evidence. Since then, a publication with the binding affinities for WF 1–5, 7–9, 11, 13, 18, 19, 22, 23, 25 has appeared (Davies, et al., *European Journal of Pharmacology—Molecular Pharmacology Section*, 1993, 244,93).

FIG. 1 compares the displacement of [$^{125}$I]RTI-55 binding by cocaine with four tropane analogs, PTT, PIT, WF-23, and WF-33. This leads to information on how these compounds bind to the dopamine transporter. These data showed that the two 2-naphthyl analogs, WF-23 and WF-33, were the most potent of these compounds, followed by PTT. PIT, in contrast, was less potent in displacing [$^{125}$I]RTI-55 than cocaine. Comparison of IC$_{50}$ values (Table 1) showed that WF-23 and WF-33 were 900 to 1300 times, while PTT was 20 times, more potent than cocaine in binding to dopamine transporters. In contrast, PIT was 2.5 times less potent than cocaine at dopamine transporters.

Figure 2:
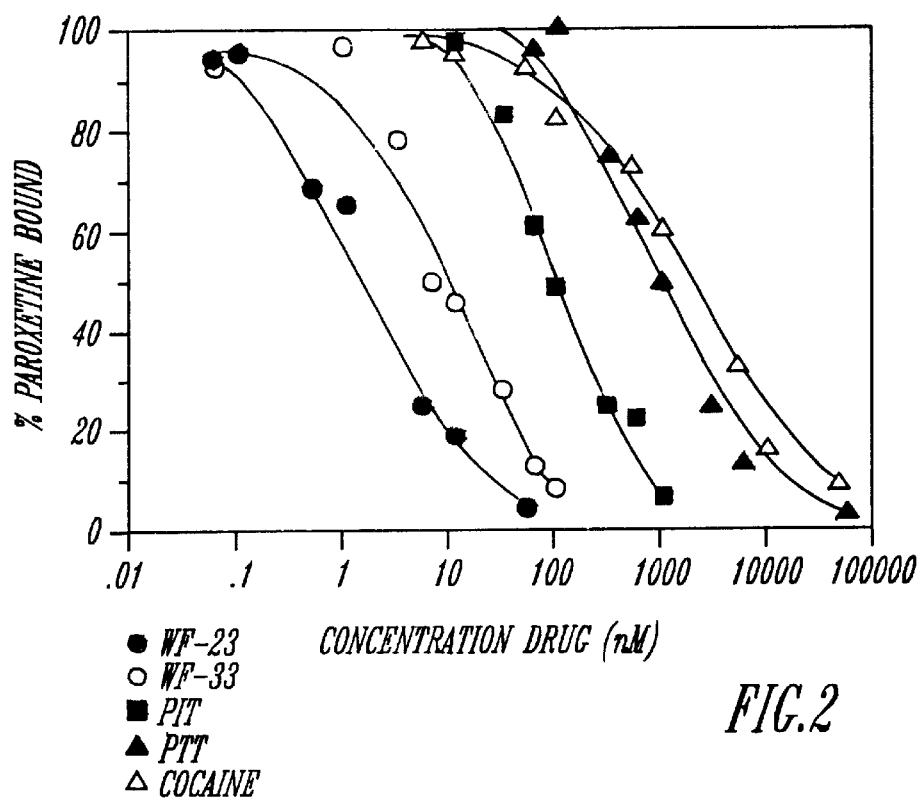

FIG. 2 shows how the selectivities of these analogs were determined in [$^3$H]paroxetine binding experiments. This leads to information on how these compounds bind to the 5-HT transporter. Again, the 2-naphthyl analogs, WF-23 and WF-33, were the most potent compounds in displacing [$^3$H]paroxetine binding, as they were vs. [$^{125}$I]RTI-55 binding (FIG. 1). However, whereas these analogs were equipotent in displacing [$^{125}$I]RTI-55 binding, WF-33 was 4 times less potent than WF-23 in displacing [$^3$H]paroxetine binding. Furthermore, the two phenyl analogs, PTT and PIT, exchanged places in displacing [$^3$H]paroxetine compared to [$^{125}$I]RTI-55; PIT was significantly more potent in displacing [$^3$H]paroxetine than cocaine, while PTT was approximately equipotent with cocaine in displacing [$^3$H]paroxetine binding (FIG. 2). IC$_{50}$ values (Table 1) showed that WF-23 and WF-33 were 480 times and 140 times, respectively, more potent than cocaine at 5-HT transporter sites, while PIT was 8 times more potent than cocaine and PTT was twice as potent as cocaine. Table 1 shows the potency ratios of all analogs in binding assays dopamine and 5-HT transporters (higher numbers demonstrate relatively greater dopamine transporter potency). These data suggested that PIT was relatively selective for 5-HT transporters, while PTT and PIT were relatively more selective for dopamine transporters. In contrast, WF-23 was like cocaine, with little selectivity between the two transporters. However, it was 500–800 times more potent than cocaine at both transporters.

The synthetic scheme that was used to produce tropane analogs from vinylcarbenoid precursors generated racemic compounds; therefore, all the binding studies discussed above were conducted with racemic compounds. When WF-23 was separated into two stereoisomers by a chiral HPLC. column, the active isomer displayed an estimated IC$_{50}$ value of 0.03 nM vs. [$^{125}$I]RTI-55, while the inactive isomer demonstrated an IC$_{50}$ value of 113 nM (see values for WF-23(1) and WF-23(2) in Table 1). These results not only demonstrated that stereoisomers can be separated by the chiral HPLC, but also shows that the active isomer is extremely potent. The active isomer of WF-23 was also potent vs. [$^3$H]paroxetine binding, and the selectivity of the active and inactive isomers were the same as the racemic mixture of WF-23. Generally those isomers with R$_2$ in the up position were more active, and as well, those compounds where R$_2$ was a ketone were more active.

Figure 3:
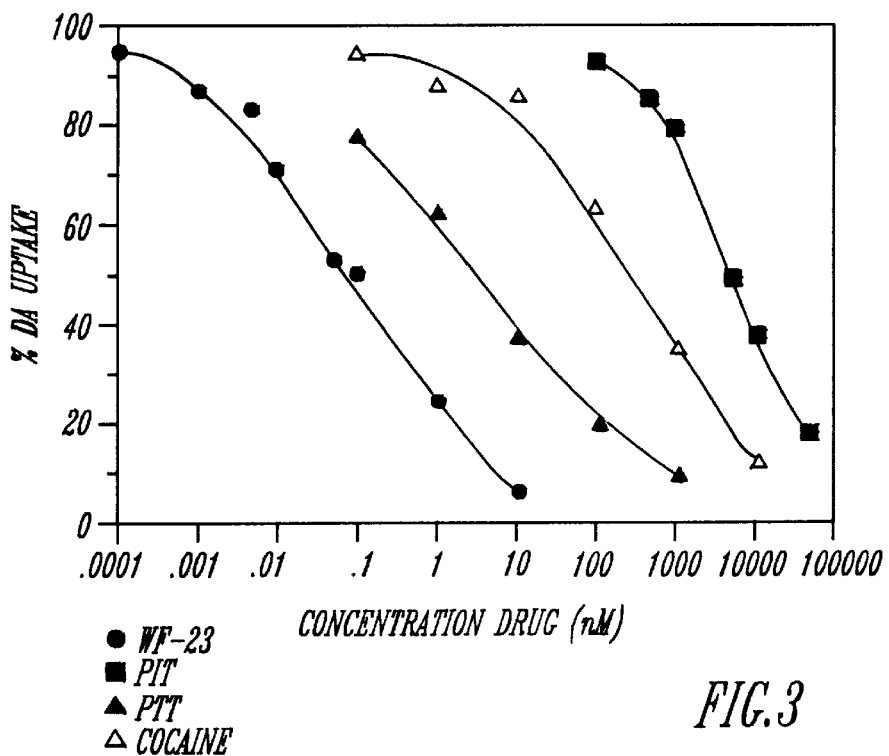
Figure 4:
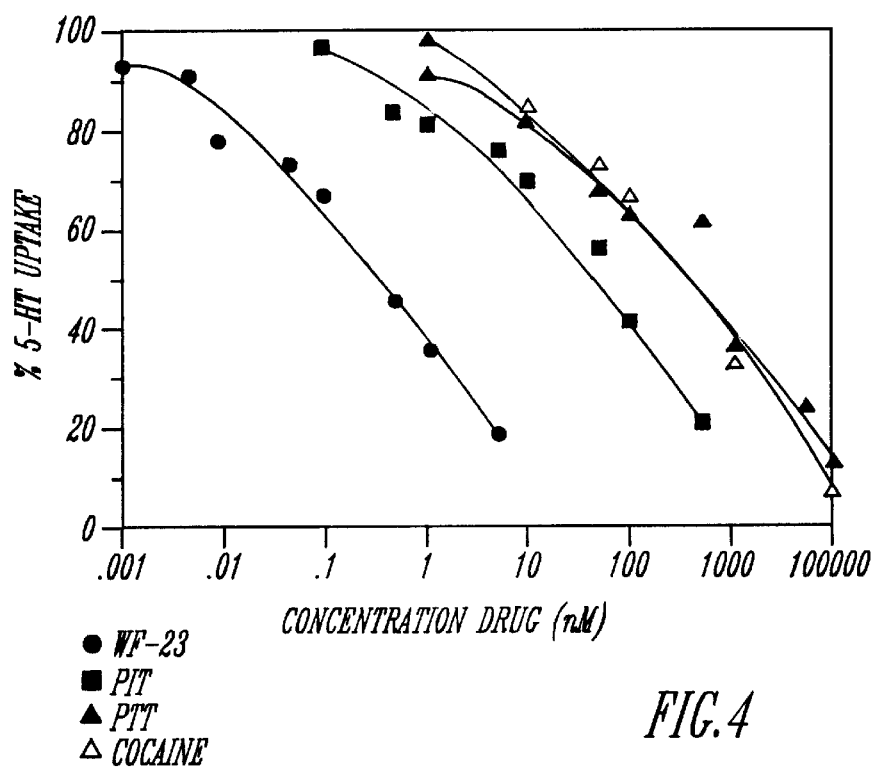

Uptake studies have been conducted on several selected analogs to confirm the results of the binding studies. These experiments utilized dissociated cells from fetal and adult rat brain, using the striatum for dopamine uptake assays, and the frontal cortex for 5-HT uptake assays. FIG. 3 shows the inhibition of [3H]dopamine uptake into striatal cells by cocaine and selected tropane analogs. These results were comparable to the binding assays: while WF-23 was the most potent analog in inhibiting dopamine uptake followed by WF-11, WF-31 was considerably less potent in blocking [3H]dopamine uptake. Experiments with [3H]5-HT uptake in cortical cells (FIG. 4) also supported the results of the binding assays, showing that WF-23 and WF-31 were both significantly more potent than cocaine in blocking [$^3$H]5-HT uptake. Thus the uptake assays confirmed the selectivities of these tropane analogs as determined in binding assays. For example, WF-11 was 140 times more potent in inhibiting dopamine uptake than 5-HT uptake, while WF-31 was 120 times more potent in inhibiting 5-HT uptake than dopamine uptake, both somewhat greater than the ratios determined by binding studies (Table 1). In contrast, WF-23, whether assayed as a racemic mixture or as its active stereoisomer, provided a dopamine: 5-HT ratio of only 3–4 regardless of the assay used.

In addition to the isopropylphenyl derivative WF-31, it is also clear that the ethylphenyl derivative WF-9, and the 1-(4-methylnapthyl) derivative WF-27 also display considerable selectivity towards the 5-HT transporter in terms of binding and inhibition. The common feature of these derivatives is that they contain a functionality that may lie to some extent in the perpendicular plane to the aromatic ring. This structural variation leads to a novel type of biological activity for compounds in the tropane series with potential for the development of a novel class of antidepressant drugs. The general activity of the group of analogs at monoamine transporter sites demonstrates that they have potential for the treatment of other diseases associated with monoamine imbalances such as Parkinson's Disease, attention-deficit hyperactivity disorder, and obesity.

What is claimed is:

1. A method of treating mammals to selectively block 5-HT uptake, said method comprising:

administering a small but effective amount of a 3-aryltropane derivative of the formula:

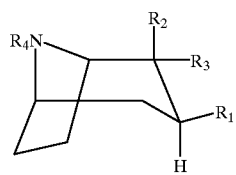

and structural isomers thereof, wherein R$_1$ is an aromatic ring moiety selected from the group consisting of 1-naphthyl, 2-naphthyl, phenyl, C$_1$ to C$_8$ alkylaryl, and indole; and R$_2$ and R$_3$ may be the same or different and are selected from the group consisting of hydrogen, C$_1$ to C$_8$ ketones, with only one of R$_2$ and R$_3$ being hydrogen at any one time and R$_4$ is methyl, hydrogen or lower alkyl.

2. The method of claim 1 where R$_2$ is a ketone.

3. The method of claim 1 wherein R$_2$ is the beta-isomer.

4. The method of claim 1 wherein the mammal is the human species.

5. The method of claim 2 wherein the administration is by a method selected from the group of oral, intravenous, and parenteral.

6. The method of claim 2 wherein the dosage is at a level of from 1 micrograms/Kg to 50 milligrams/Kg.

7. The method of claim 2 wherein the dosage is oral at a level of from 20 micrograms/Kg to 15 mg/Kg.

8. A method of treating mammals to selectively block 5-HT uptake, said method comprising:

administering a small but treatment effective amount of a 3-aryltropane derivative of the formula:

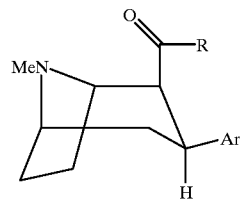

and structural isomers thereof wherein R equals C$_1$ to C$_8$ alkyl and Ar is an aromatic ring moiety, to said mammals.

9. A method of treating mammals to selectively block Dopamine uptake, said method comprising:

administering a small but effective amount of a 3-aryltropane derivative of the formula:

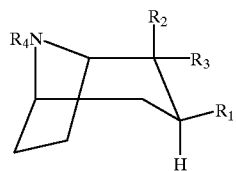

and structural isomers thereof, wherein R$_1$ is an aromatic ring moiety selected from the group consisting of 1-naphthyl, 2-naphthyl, phenyl, C$_1$ to C$_8$ alkylaryl, and indole; and $R_2$ and $R_3$ may be the same or different and are selected from the group consisting of hydrogen, $C_1$ to $C_8$ ketones, with only one of $R_2$ and $R_3$ being hydrogen at any one time;

$R_4$ is methyl, hydrogen or lower alkyl.

10. The method of claim 9 where $R_2$ is a ketone.

11. The method of claim 9 wherein $R_2$ is the isomer with $R_2$ in the beta-position.

12. The method of claim 9 wherein the mammal is the human species.

13. The method of claim 10 wherein the administration is by a method selected from the group of oral, intravenous, and parenteral.

14. The method of claim 10 wherein the dosage is at a level of from 1 micrograms/Kg to 50 milligrams/Kg.

15. The method of claim 10 wherein the dosage is oral at a level of from 20 micrograms/Kg to 15 mg/Kg.

16. A method of treating mammals to selectively block 5-HT uptake, said method comprising: administering a small but treatment effective amount of a 3-aryltropane derivative of the formula:

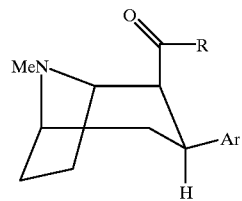

and structural isomers thereof wherein R equals $C_1$ to $C_8$ alkyl and Ar is an aromatic ring moiety, to said mammals.

* * * * *